(12) United States Patent
Ramasamy

(10) Patent No.: US 6,525,191 B1
(45) Date of Patent: Feb. 25, 2003

(54) CONFORMATIONALLY CONSTRAINED L-NUCLEOSIDES

(76) Inventor: Kanda S. Ramasamy, ICN Pharmaceuticals, Inc., 3300 Hyland Ave., Costa Mesa, CA (US) 92626

( * ) Notice: Subject to any disclaimer, the term of this patent is extended or adjusted under 35 U.S.C. 154(b) by 0 days.

(21) Appl. No.: 09/569,183

(22) Filed: May 11, 2000

Related U.S. Application Data

(60) Provisional application No. 60/133,551, filed on May 11, 1999.

(51) Int. Cl.$^7$ .................. C07H 19/056; A61K 31/70; C12Q 1/68
(52) U.S. Cl. .................. 536/28.7; 514/43; 514/49; 435/6
(58) Field of Search .............. 514/45, 50, 49, 514/43; 435/6, 91.1; 336/26, 24; 536/28.7

(56) References Cited

U.S. PATENT DOCUMENTS

| | | | |
|---|---|---|---|
| 5,627,160 A | * 5/1997 | Lin et al. | 514/49 |
| 5,631,239 A | * 5/1997 | Lin et al. | 514/29 |
| 5,672,594 A | * 9/1997 | Weis et al. | 514/45 |
| 5,747,252 A | * 5/1998 | Yang et al. | 435/6 |
| 6,130,326 A | * 10/2000 | Ramasamy et al. | 536/28.7 |

FOREIGN PATENT DOCUMENTS

| | | | |
|---|---|---|---|
| WO | WO99/14226 | 3/1999 | C07H/21/00 |

OTHER PUBLICATIONS

Kvrno, et al. "Novel Bicyclic Nucleoside Analogue (1S,5S, 6S)–6–Hydroxy–5–hydroxy–1–(uracil–1–yl)–3–8–dioxabicyclo[3.2.1]octane:Synthesis and Incorporation into Oligodeoxynucleotides", J. Org. Chem., 66(16), 2001, pp5498–5503.*

Zhang, w., et al, "An improved synthesis of 2'–deoxy–L–ribose." Book of Abstracts, 217$^{th}$ ACS National Meeting, Anaheim CA, Mar. 21–25, (1999) CARB–050. American Chemical Society, Washington DC, Coden: 67GHA6.*

Christensen, N.K. et al., A Novel class of Oligonucleotide Analogues Containing 2'–O,3'–c–ILinked [3.2.0]Bicycloarabinonucleoside Monomers: Synthesis, Thermal Affinity Studies, and Molecular Modeling. J. Am. Chem. Soc., 1998, 120, 5458–5463.*

Koshkin, A. a., et al., LNA (Locked Nucleic Acid): An RNA mimic Forming Exceedingly Stable LNA:LNA Duplexes. J. Am. Chem. Soc., 1998, 120, 13252–13253.*

Kool, E. T., et al., Preorganization of DNA: Design Principles for Improving Nucleic Acid Recognition by Synthetic Oligonucleotides. Chem. Rew., 1997, 97, 1473–1487.*

Wang, G., et al Conformationally Locked Nucleosides. Synthesis and Hybridazation Properties of Oligodeoxynucleotides containg 2',4'–C–Bridged 2'–Deoxynucleosides, Bioorg. and Med. Chem Lett., 1999, 9 (66), pp 5498–5503.*

Obika, S., etal., Stability and Structural Features of the Duplexes Containing Nucleoside Analogues with N–Type Conformation, 2'–O,4'–C–methyleneribonucleosides., Tetrahedron Lett. 39 (1998) pp5401–5404.*

Obika, S., etal., Synthesis of 2'–O,4'–C–methyleneuridine and –cytidine. Novel Bicyclic Nucleosides Having A fixed C3, –endo Sugar Puckering., Tetrahedron Lett. 38(50), (1998) pp10322–7.*

Wang, G., et al., Conformationally Locked Nucleosides. Synthesis and Stereochemical Assignments of 2'–C4'–Bridged Bicyclonucleosides., Tetrahedron 55 (1999) pp7707–7724.*

Wang, G., et al., LNA (Locked Nucleic Acids): Synthesis of the Adenine, Cytosine, Guanine, 5–Methylcytosine, Thymine and Uracil Bicyclonucleosides Monomers, Oligomerisation, and Unpresecendate Nucleic Acid Recoignation., Tetrahedron 54 (1998) pp3607–3630.*

* cited by examiner

*Primary Examiner*—Jeffrey Fredman
*Assistant Examiner*—Christine Maupin
(74) *Attorney, Agent, or Firm*—Rutan & Tucker, LLP; Robert D. Fish

(57) ABSTRACT

L-nucleosides are conformationally constrained by at least one additional ring formed by a bridge connecting at least two atoms within a sugar moiety of the nucleoside. While a single additional ring is formed by bridging $C_1$–$C_4$ atoms, two additional rings are formed by bridging both $C_1$–$C_2$, and $C_3$–$C_4$ atoms, or $C_1$–$C_3$ and $C_2$–$C_4$ atoms by bridges having the general structure A—B—Z. The conformationally constrained nucleosides may be incorporated into oligonucleotides and dinucleotides, and it is contemplated that compositions including the conformationally constrained nucleosides may have superior viral inhibitory or antineoplastic properties.

6 Claims, 9 Drawing Sheets

Scheme 4

Scheme 5

Scheme 6

Scheme 7

Scheme 8

CONFORMATIONALLY CONSTRAINED L-NUCLEOSIDES

This application claims the benefit of U.S. provisional application No. 60/133,551 filed May 11, 1999, incorporated herein by reference in its entirety.

FIELD OF THE INVENTION

The present invention relates to novel nucleosides and oligonucleotides having conformationally constrained sugar moieties.

BACKGROUND OF THE INVENTION

Nucleosides derived from natural D-ribose play a significant role for the treatment of human viral diseases, neoplastic diseases, and modulation of immune response. Among them, Ribavirin (1-beta-D-ribofuranosyl-1,2,4-triazole-3-carboxamide), AZT (3'-azido-3'-deoxythymidine), ddI (2',3'-dideoxyinosine), and ddC (2',3'-dideoxycytidine) are among the most prominent drugs presently approved. Despite their relatively potent antiviral and antineoplastic activity, emerging resistance of many viruses and tumor cells prompted a search for new nucleosides.

In addition to nucleosides derived from D-ribose, novel nucleosides employing sugars in L-conformation have been proposed as antiviral agents, and several L-nucleosides appear to have significant biological activity at lower toxicity than their counterpart D-nucleosides. The most active L-nucleosides reported to date include L-T (L-thymidine), 3TC (L-3'-thiacytidine), FTC (L-5-fluoro-3'-thiacytidine), L-ddC (L-2',3'-dideoxycytidine), and L-FddC (L-5-fluoro-2',3'-dideoxycytidine).

Furthermore, variations of D-nucleosides with novel sugar and sugar-like rings have been developed by introducing different heterocyclic moieties. For example, the replacement of a furanose ring with 1,3-dioxolane, 1,3-oxathiolane, 4'-thio heterocylic moieties has produced potent anti-viral compounds. Nucleosides containing tetrahydrothiophene, isoxazole, oxazolidine, thiazolidine and pyrrolidine ring systems instead of D-ribose are also known. Furthermore, an L-nucleoside analog (3TC) containing a non-ribose heterocyclic moiety has been approved for the treatment of human immunodeficiency virus (HIV) replication and hepatitis B virus (HBV) propagation.

More recently, bicyclic D-nucleosides have been prepared and found to be inhibitors of HIV reverse transcriptase [V. E. Marquez et al., *J. Med. Chem.*, 20, 2780–2789, 1998]. Additionally, bicyclic D-nucleosides have been incorporated into oligonucleotide sequences and screened as anti-sense agents [S. Obika et al., *Tetrahedron Letts*, 39, 5401–5404, 1998]. Wengel and Nielsen described in their international patent application WO 99/14226 oligonucleotides with bicyclic D-nucleotides having additional rings in various positions.

There are, however, no reports on conformationally constrained bi-, and tricyclic L-nucleosides. Therefore, there is a need to provide methods and compounds for conformationally constrained bi-, and tricyclic L-nucleosides.

SUMMARY OF THE INVENTION

The present invention is directed to conformationally constrained L-nucleosides of the general structure as shown below.

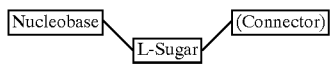

The nucleobase generally includes natural and non-natural bases, and the L-sugar includes a natural or non-natural sugar in L-configuration having at least one additional cyclic structure (i.e., ring) formed by a bridge having the general structure A—B—Z. An optional connector moiety may be covalently bound to the L-sugar, and where a connector moiety is present, the connector and the nucleobase are separated by at least one atom in the sugar. While in some preferred conformationally constrained L-nucleosides a single additional ring is formed by bridging the $C_1$–$C_4$, $C_1$–$C_2$, $C_1$–$C_3$, $C_2$–$C_4$, or $C_3$–$C_4$ atoms, other nucleosides may have two additional rings by bridging both the $C_1$–$C_2$, and the $C_3$–$C_4$ atoms, or both the $C_1$–$C_3$ and the $C_2$–$C_4$ atoms.

In one aspect of the inventive subject matter, the conformationally constrained nucleosides have a structure as generally depicted in Structures I–IX. The Base is a nucleobase covalently bound to the $C_1$-atom via a nitrogen- or carbon atom in the nucleobase and is preferably a substituted or unsubstituted purine or pyrimidine base, a substituted or unsubstituted imidazole, pyrazole, pyrrole, or triazole. X is typically oxygen, but may also be substituted with alternative heteroatoms, including substituted and unsubstituted sulfur, nitrogen, carbon, and selenium. In structure IV, E, F, and G are typically —$CH_2$— or —$C(H)(OH)$—, and the bridge elements A, B, and Z are independently substituted or unsubstituted carbon, lower (i.e., with up to 5 carbon atoms) branched or unbranched alkyl or alkenyl, or substituted or unsubstituted heteroatoms, including oxygen, sulfur, and nitrogen. Contemplated optional connectors include bi- and multifunctional groups such as mono-, di-, and triphosphate groups, diacids, diamides, etc., and are preferably covalently connected to any one of $R_1$–$R_4$, A, B, and Z. $R_1$–$R_4$ are independently nothing, H, OH, substituted and unsubstituted sulfur, nitrogen, carbon or phosphorus. Depending on the individual substituents, the conformationally constrained L-nucleoside may be electrically neutral, charged or in a salt form with an appropriate salt.

Structure I

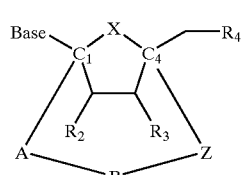

Structure II

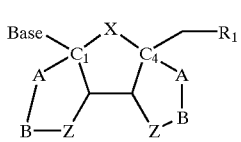

Structure III

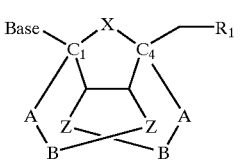

-continued

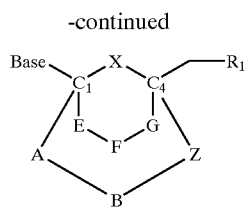

Structure IV

In more preferred aspects of structures I–IX, X is O, S. CHOH, CH$_2$ or N—COCH$_3$, A is O, S, (CH$_2$)$_n$, N—R, or nothing, and B and Z are independently O, S, (CH$_2$)$_n$, or N—R. When both B and Z are independently O, S or N—R then A is (CH$_2$)$_n$, and when both A and B are independently O, S or N—R then Z is (CH$_2$)$_n$, wherein R is H, OH, CO—, lower alkyl or COCH$_3$, and n is 1–5. It is also preferred that no more than two of A, B, and Z are an atom other than a carbon atom. R$_2$ and R$_3$ are independently H, OH, OPO$_3^{2-}$, CN, halogen, N$_3$, CH$_2$OH, methylidene, lower alkyl or lower alkyl amine, and R$_1$ and R$_4$ is H, OH, OPO$_3^{2-}$. In structure IV, E is preferably O, S, (CH$_2$)$_n$, N—R, or nothing, and F and G are independently O, S, (CH$_2$)$_n$, or N—R. When both F and G are independently O, S or N—R then E is (CH$_2$)$_n$, and when both E and F are independently O, S or N—R then G is (CH$_2$)$_n$, wherein R is H, OH, CO—, lower alkyl or COCH$_3$, and n is 1–5; and wherein no more than two of E, F, and G are an atom other than a carbon atom. In both general and preferred structures I–IX, all structures are excluded in which the nucleobase or any of the substituents A, B, Z, X, and R$_1$–R$_4$ are in charge, sterical, stereoelectronic or other structural conflict.

In another aspect of the inventive subject matter, nucleosides according to structures II and III may have only one additional ring in which a bridge of the general structure —A—B—Z— covalently connects the carbon atoms C$_1$ and C$_2$, or C$_3$ and C$_4$ in structure II, or carbon atoms C$_1$ and C$_3$, or C$_2$ and C$_4$ in structure III. Where nucleosides according to structure III have only a single additional ring, it is preferred that A and Z are nothing and B is a methylene group.

In a further aspect of the inventive subject matter, the nucleoside is covalently coupled to at least one nucleotide to form a modified oligonucleotide or modified dinucleotide. Although preferred nucleosides have an L-configuration, alternative nucleosides may also have a D-configuration.

Various objects, features, aspects and advantages of the present invention will become more apparent from the following detailed description of preferred embodiments of the invention, along with the accompanying drawing.

DETAILED DESCRIPTION

Figure 1A:
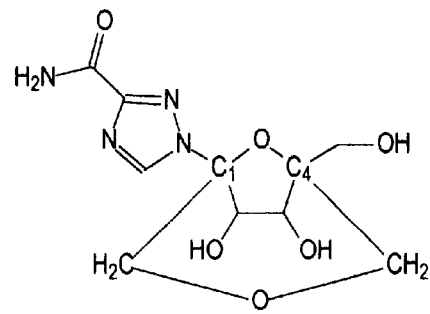
FIGS. 1A–1I show exemplary structures of conformationally constrained nucleosides according to the inventive subject matter.
Figure 1B:
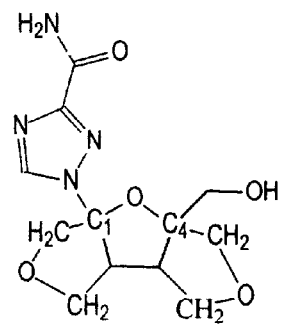
Figure 1C:
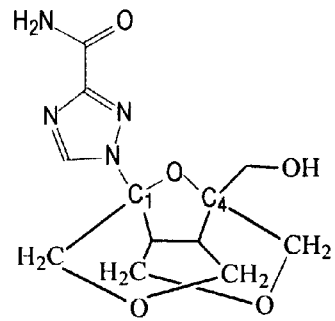
Figure 1D:
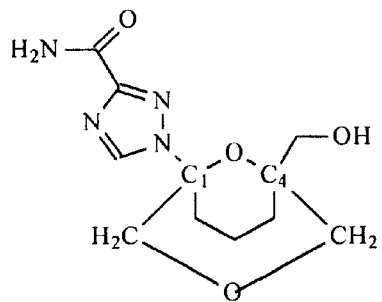
Figure 1E:
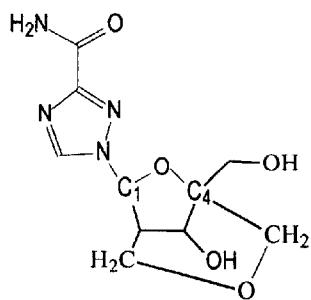
Figure 1F:
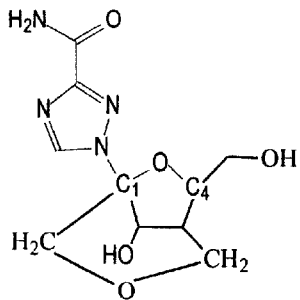
Figure 1G:
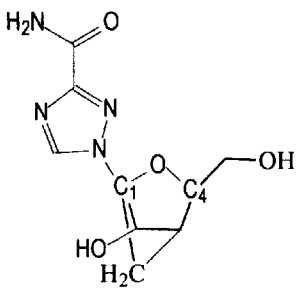
Figure 1H:
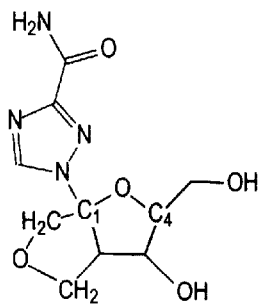
Figure 1I:
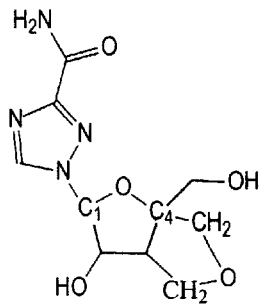
Figure 2A:
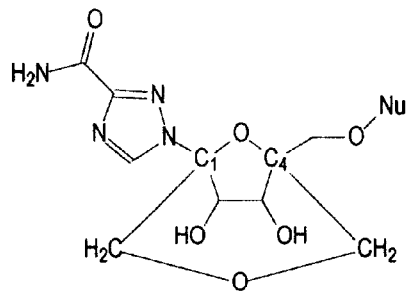
FIGS. 2A–2I show exemplary structures of conformationally constrained nucleosides covalently coupled to a nucleotide according to the inventive subject matter.
Figure 2B:
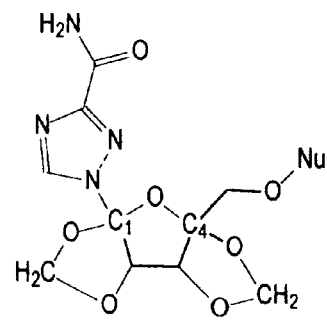
Figure 2C:
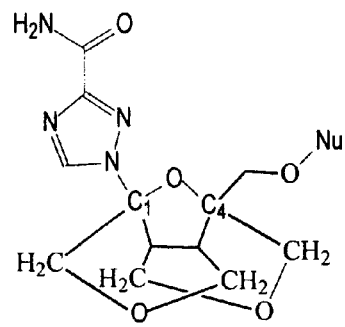
Figure 2D:
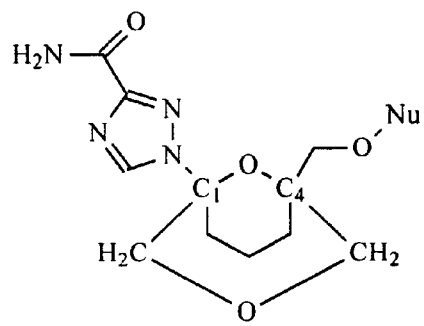
Figure 2E:
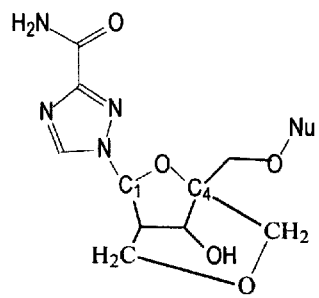
Figure 2F:
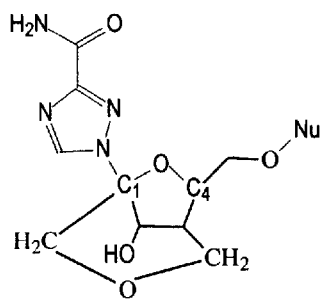
Figure 2G:
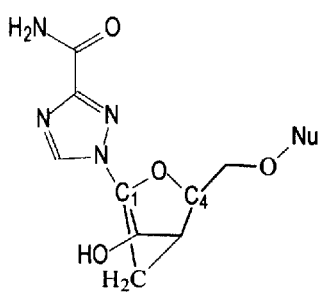
Figure 2H:
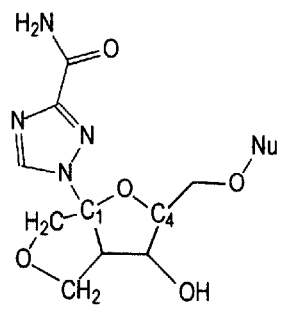
Figure 2I:
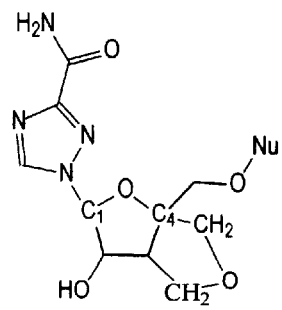

As used herein, the term "nucleoside" refers to a molecule in which a nucleobase is glycosidically linked to a sugar or sugar-like ring. While nucleobases preferably include substituted or unsubstituted purine or pyrimidine bases, substituted or unsubstituted imidazoles, pyrazoles, pyrroles, or triazoles are also contemplated.

The term "nucleotide" as used herein generally refers to nucleosides that carry at least one covalently coupled phosphate or phosphate-like moiety. Phosphate moieties are typically mono-, di-, and triphosphates, and phosphate-like moieties include phosphate groups in which one or more atoms (e.g., oxygen) may be substituted with other atoms (e.g., sulfur), and, while not limiting to the inventive subject matter, contemplated phosphate or phosphate-like moieties preferably have a trigonal bipyramidal configuration.

As also used herein, the term "oligonucleotide" refers to a plurality of nucleotides that are covalently coupled together. Especially contemplated oligonucleotides include oligonucleotides having a sugar phosphate backbone with a polarity (e.g., 5'->3'), however, various alternative linear, branched or non-linear oligonucleotides are also contemplated. The term "dinucleotide" refers to a molecule in which two nucleotides are covalently coupled to each other via at least one phosphate or phosphate-like group, and preferred dinucleotides comprise an adenine nucleotide.

As further used herein, the term "conformationally constrained" molecule means that at least one of a rotational or translational degree of freedom is reduced or eliminated in the molecule. Consequently, conformationally constrained molecules may be locked in a particular conformation (e.g., endo conformation of ribofuranose), or may have one or more substituents confined to a particular conformation and/or position with respect to the remainder of the molecule.

In Structure I, a conformationally constrained bicyclic nucleoside generally has a sugar moiety (i.e., a sugar or sugar-like ring) in L-configuration to which a nucleobase and an R$_4$ group are bound via the C$_1$ and C$_4$ atom, respectively. C$_1$ and C$_4$ atoms are further bridged via bridge —A—B—Z—, and C$_2$ and C$_3$ have substituents R$_2$ and R$_3$.

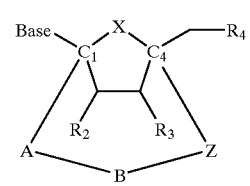

Structure I

In a preferred aspect of the inventive subject matter, the nucleobase is a 1,2,4-triazole-3-carboxamide, which is covalently bound via an N-glycosidic bond to a beta-L-ribofuranose sugar moiety. R$_2$, R$_3$, and R$_4$ are preferably OH. A and Z are preferably methylene, and B is preferably a heteroatom.

In Structure II, a conformationally constrained tricyclic nucleoside generally has a sugar moiety (i.e., a sugar or sugar-like ring) in L-configuration to which a nucleobase and a $R_1$ group are bound via the $C_1$ and $C_4$ atom, respectively. The $C_1$ and $C_2$ atoms as well as the $C_3$ and $C_4$ atoms are further bridged via bridge —A—B—Z—.

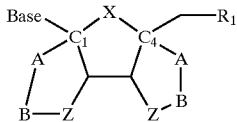

Structure II

In a preferred aspect of the inventive subject matter, the nucleobase is a 1,2,4-triazole-3-carboxamide, which is covalently bound via an N-glycosidic bond to a beta-L-ribofuranose sugar moiety. $R_1$ is preferably OH, A and Z are preferably methylene, and B is preferably a heteroatom.

In Structure III, a conformationally constrained tricyclic nucleoside generally has a sugar moiety (i.e., a sugar or sugar-like ring) in L-configuration to which a nucleobase and a $R_1$ group are bound via the $C_1$ and $C_4$ atom, respectively. Both, $C_1$ and $C_3$ atoms, and $C_2$ and $C_4$ atoms are further bridged via bridge —A—B—Z—.

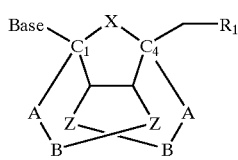

Structure III

In a preferred aspect of the inventive subject matter, the nucleobase is a 1,2,4-triazole-3-carboxamide, which is covalently bound via an N-glycosidic bond to a beta-L-ribofuranose sugar moiety. $R_1$ is preferably OH, A and Z are preferably methylene, and B is preferably a heteroatom.

In Structure IV, a conformationally constrained bicyclic nucleoside generally has a sugar moiety (i.e., a sugar or sugar-like ring) in L-configuration to which a nucleobase and a $R_1$ group are bound via the $C_1$ and $C_4$ atom, respectively. $C_1$ and $C_4$ atoms are bridged via bridge —A—B—Z—.

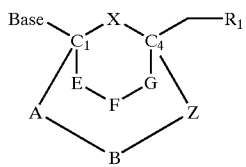

Structure IV

In a preferred aspect of the inventive subject matter, the nucleobase is a 1,2,4-triazole-3-carboxamide, which is covalently bound via an N-glycosidic bond to a beta-L-glucopyranose sugar moiety. $R_1$ is preferably OH, A and Z are preferably methylene, and B is preferably a heteroatom.

In Structures V and VI, a conformationally constrained bicyclic nucleoside generally has a sugar moiety (i.e., a sugar or sugar-like ring) in L-configuration to which a nucleobase and a $R_1$ group are bound via the $C_1$ and $C_4$ atom, respectively. $C_1$ and $C_3$ atoms (in structure V) or $C_2$ and $C_4$ atoms (in structure VI) are further bridged via bridge —A—B—Z—.

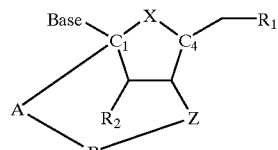

Structure V

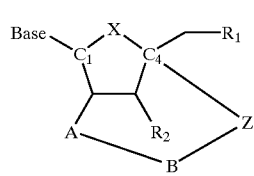

Structure VI

In a preferred aspect of the inventive subject matter, the nucleobase is a 1,2,4-triazole-3-carboxamide, which is covalently bound via an N-glycosidic bond to a beta-L-ribofuranose sugar moiety. $R_1$ and $R_2$ are preferably OH, A and Z are preferably methylene, and B is preferably a heteroatom.

In Structure VII, a conformationally constrained bicyclic nucleoside generally has a sugar moiety (i.e., a sugar or sugar-like ring) in L-configuration to which a nucleobase and a $R_1$ group are bound via the $C_1$ and $C_4$ atom, respectively. A methylene group connects the carbon atoms $C_1$ and $C_3$.

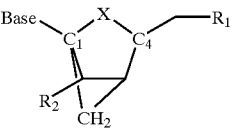

Structure VII

In a preferred aspect of the inventive subject matter, the nucleobase is a 1,2,4-triazole-3-carboxamide, which is covalently bound via an N-glycosidic bond to a beta-L-ribofuranose sugar moiety. $R_1$ and $R_2$ are preferably OH.

In Structures VIII and IX, a conformationally constrained bicyclic nucleoside generally has a sugar moiety (i.e., a sugar or sugar-like ring) in L-configuration to which a nucleobase and a $R_1$ group are bound via the $C_1$ and $C_4$ atom, respectively. $C_1$ and $C_2$ atoms (in structure VIII) and $C_3$ and $C_4$ atoms (in structure IX) are further bridged via bridge —A—B—Z—.

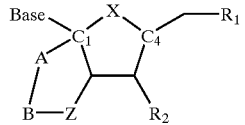

Structure VIII

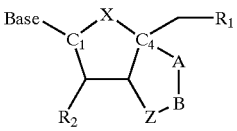

Structure IX

In a preferred aspect of the inventive subject matter, the nucleobase is a 1,2,4-triazole-3-carboxamide, which is covalently bound via an N-glycosidic bond to a beta-L-ribofuranose sugar moiety. $R_1$ and $R_2$ are preferably OH, A and Z are preferably methylene, and B is preferably a heteroatom. Exemplary constrained nucleosides are depicted in FIGS. 1A–1I.

It is generally contemplated that conformationally constrained bicyclic and tricyclic nucleosides may have various sugar moieties other than a beta-L-Ribose and a beta-L-glucopyranose, and alternative sugar moieties include various furanose and pyranose sugars, carbocyclic furanose and pyranose sugar analogs, and non-sugar moieties with 5- and 6-membered rings, including dioxane, tetrahydropyrane, tetrahydrofurane, etc. For example, where antisense-oligonucleotides comprise one or more contemplated nucleosides, it is preferred that sugar moieties have a beta-L-configuration to facilitate correct hybridization, and particularly preferred furanose sugars include beta-L-ribofuranose, beta-L-xylofuranose, beta-L-arabinofuranose, while particularly preferred pyranose sugars include beta-L-glucopyranose, beta-L-fructopyranose, and beta-L-galactopyranose. It is further contemplated that alternative sugar moieties may also comprise a heteroatom other than oxygen, and particularly contemplated heteroatoms include substituted sulfur and nitrogen (e.g., $SO_2$, N—$COCH_3$). For example, heteroatoms may be included to provide an atom within the sugar moiety to which additional chemical groups may be attached. An addition of a nitrogen may be especially advantageous where the heteroatom may carry an electrical charge (e.g., $N^+$). Alternatively, contemplated sugar and sugar-like rings may have a substituted or unsubstituted carbon atom instead of a heteroatom (e.g., carbocyclic sugars). Carbon atoms advantageously reduce polarity in the sugar moiety, and provide a substituent that lacks additional free electron pairs (as compared to oxygen or sulfur), and especially contemplated carbon atoms include $CH_2$ and CHOH groups.

It should be appreciated that the choice of a particular sugar moiety is predominantly determined by the type of biochemical interaction and/or steric environment of a target molecule with contemplated conformationally constrained nucleosides. The term "target molecule" as used herein refers to any molecular entity that interacts with the conformationally constrained nucleoside via electrostatic, ionic, hydrophilic, or hydrophobic interaction or via formation of one or more hydrogen bonds. Thus, target molecules include allosteric, competitive and non-competitive binding to a protein (e.g., enzyme, repressor, hormone responsive element, etc.), natural or synthetic DNA and/or RNA and their analogs, etc. For example, where the nucleoside is employed as an enzyme inhibitor the stereochemical requirements of the sugar or sugar-like ring may vary. For example, inhibitors of the IMPDH (inosine monophosphate dehydrogenase) tend to require less stringent requirements with respect to the sugar moiety to achieve at least some effect. Therefore, a broader variety of appropriate sugars and/or sugar-like rings may be utilized. In contrast, other enzymes (e.g., viral DNA and/or RNA polymerases) may discriminate more stringently among inhibitors with alternative sugar moieties. Alternatively, where the nucleoside is integrated into an oligonucleotide, furanose and carbocyclic furanose moieties may advantageously replace a ribofuranose, which may consequently lead to increased melting points in DNA/DNA and DNA/RNA heteroduplexes and heterotriplexes. While it is generally preferred that the sugar and sugar-like rings are in an L-configuration, it is also contemplated that alternative sugar and sugar-like rings may be in a D-configuration (e.g., D-ribose, D-fructose).

Consequently, depending on the particular nature and configuration of appropriate sugars and sugar-like rings, the groups $R_1$–$R_4$ may vary considerably. Contemplated groups $R_1$–$R_4$ may therefore include non-carbon groups such as H, OH, $OPO_3^{2-}$, or halogens, but also carbon containing groups such as methyl-, methoxy-, acetyl-, or methylidene groups. It is particularly preferred that where the $C_2$ atom and/or $C_3$ atom have a carbon containing substituent, spiro rings may be attached to either or both of the $C_2$ and $C_3$ atoms, and contemplated spiro rings may thereby comprise two to about eight carbon or non-carbon atoms.

With respect to the nucleobase, it is contemplated that a broad variety of nucleobases may be employed in conjunction with the teachings presented herein, including substituted or unsubstituted purine or pyrimidine bases, substituted or unsubstituted imidazoles, pyrazoles, pyrroles, and triazoles. For example, unsubstituted purine or pyrimidine bases may be especially advantageous where the conformationally constrained nucleoside is incorporated into a single-, or double stranded DNA or RNA under retention of the natural bases. Particularly contemplated unsubstituted purine or pyrimidine bases include adenine, guanine, thymine, cytosine, uracil. Where higher chemical stability and stronger interstrand interactions are desirable, modified and/or substituted purine or pyrimidine bases may be employed, including aza-, deaza-, and thio-nucleotides. Particularly conemplated modified and/or substituted purine bases are 8-azapurine, 8-azaguanine, 6-azapyrimidine, 7-deazapurine, 3-deazapurine, 7-deazaguanine, 3-deazaguanine, 6-thioguanine, 6-thiopurine. Further contemplated alternative nucleobases include triazolopurines, imidazolopurines, pyrrolopurines, pyrazolopurines, 2-aminoadenine, 3-carbaadenine, 1-carbaadenine, 7-carbaadenine, 6-hydroxypurine, 2-amino-6-chloropurine, 2-amino-6-methylpurine, 2-amino-6-hydroxypurine, 2-methylguanine, 3-carba-6-chloropurine. Especially contemplated modified and/or substituted pyrimidine bases are 5-azacytidine, 5-azauracil, triazolopyridinyl, imidazolopyridinyl, pyrrolopyimidinyl, pyrazolopyrimidinyl, 6-substituted pyrimidines, 5-fluorouracil, 5-chorouracil, 5-fluorocytosine, pseudouracil, 1-methylpseudouracil, 3-methylcystosine, 5-methylcytosine, 5-substituted uracil such as 5-methyluracil, 5-cyanouracil, and 5-acetyleneuracil, 6-azauracil and 6-carbomethoxyuracil.

Alternatively, where conformationally constrained nucleosides are employed as enzyme inhibitors (e.g., dinucleotide dependent enzymes or enzymes involved in nucleotide synthesis), substituted and unsubstituted imidazoles, pyrazoles, pyrroles, or triazoles may be utilized,- including 1,2,3-triazoles, methyl-1,2,4-triazole-3-carboxylate, etc.

In a further aspect of the inventive subject matter, the bridge structure —A—B—Z— forming the additional ring or rings on the sugar or sugar-like ring (i.e., bridging of the $C_1$ -$C_4$ atoms, C $_1$–$C_2$ and $C_3$–$C_4$ atoms, or $C_1$–$C_3$ and $C_2$–$C_4$ atoms) need not be limited to —$CH_2$—O—$CH_2$—, but may include various atoms other than oxygen and a:methylene group, including substituted or unsubstituted sulfur, nitrogen, or $(CH_2)_n$, with n=1–5. While it is generally preferred that alternative bridges have the general structure —A—B—Z—, A may be nothing and therefore bridges of the general structure —B—Z— are also contemplated.

With respect to the size of bridge, it should be appreciated that the size of the bridge may vary considerably depending on the required constraint of the nucleoside. For example, a lower degree of flexibility (i.e., a higher constraint) typically demands a shorter bridge, which may include a bridge of the structure —B—Z— or —A—B—Z— with no more than 5–7 atoms. On the other hand, where additional stabilization is desirable, larger bridges having a general —A—B—Z— structure with 8–15 atoms or more are contemplated. Particularly contemplated substituents for A, B, and Z include $(CH_2)_n$, N—R with R=H, OH, CO, lower alkyl, $COCH_3$, —$CH(CH_3)_3$—, etc. It is further contemplated that double bonds between A and B and/or between B and Z may further reduce flexibility, and it is particularly contemplated that the double bonds may be conjugated.

With respect to the chemical composition (i.e., the substituents for A, B, and Z) of the bridge it is contemplated that appropriate substituents may include electron orbitals that are not involved in the formation of a chemical bond (e.g., 2 free electron orbitals in —O—). Such orbitals may further restrict flexibility in the nucleoside by attractive or repelling electrostatic interaction. For example, where the substituent B in the bridge is oxygen and the heteroatom X in the sugar moiety is an ammonium cation, attractive electrostatic interaction may stabilize a particular conformation of the nucleoside.

It should further be appreciated that constraint in the nucleosides may also depend on the number and position of bridges in the nucleoside. For example, a single bridge connecting $C_1$ and $C_4$ atom may constrain the conformation in a particular conformation (e.g., in endo-conformation). Alternatively, two bridges may connect $C_1$ with $C_2$ and $C_3$ with $C_4$, or connect $C_1$ with $C_3$ and $C_2$ with $C_4$ to stabilize another sugar configuration. It is further contemplated that where two bridges are attached to the sugar or sugar-like ring, size and chemical composition need not necessarily be identical, but may vary substantially.

It is generally contemplated that conformational constrained nucleosides exhibit significantly altered biochemical properties that may find advantageous use in various circumstances. For example, conformationally constrained nucleosides may be incorporated into oligonucleotides to increase the melting point of DNA/DNA or DNA/RNA heteroduplexes and heterotriplexes. Oligonucleotides with increased melting points are particularly desirable where thermal stability of hybridization products is required (e.g., high stability antisense oligonucleotides). Such oligonucleotides may have a reduced number of nucleotides at comparable thermal stability when compared to oligonucleotides without conformationally constrained nucleosides. Furthermore, such oligonucleotides may have significantly increased stability at comparable temperature when compared to oligonucleotides without conformationally constrained nucleosides. Incorporation of the constrained nucleoside may occur on at least one of a 5' and 3' end, but may also occur within an oligonucleotide that may comprise naturally occurring nucleotides, but also modified and unnatural nucleotides. In particular, it is contemplated that incorporation of the constrained nucleoside involves at least one of $R_1$–$R_4$ (e.g., via esterification where $R_1$–$R_4$ is OH), E, F, G, or B (e.g., via amide bond where E, F, G, and B comprise N—R). FIGS. 2A–2I depict exemplary constrained nucleosides incorporated into an oligonucleotide wherein Nu is an oligonucleotide covalently coupled to the constrained nucleoside via a 3'-phosphate group of the oligonucleotide.

In another aspect of the inventive subject matter, it is contemplated that conformationally constrained nucleosides may be employed as a direct antiviral agent. For example, conformationally constrained nucleosides may have antiviral activity as reverse transcriptase inhibitors by a variety of mechanisms, including chain termination, allosteric, competitive or non-competitive inhibition. For example, while conformationally constrained nucleosides according to Structures II and III may act as chain terminating substrates lacking a 2'- and 3'-OH function, nucleosides according to Structures I and IV may act as competitive inhibitory substrates for a viral reverse transcriptase.

In a further aspect, it is contemplated that conformationally constrained nucleosides may be employed as an antineoplastic and/or immunomodulatory agent. Particularly contemplated nucleosides include a triazole carboxamide as a nucleobase and a L-ribose as a sugar moiety and have at least one additional ring formed by at least one bridge, thereby structurally resembling the. L-isomer of ribavirin (1-beta-D-ribofuranosyl-1,2,4-triazole-3-carboxamide), a compound known to have antineoplastic and immunomodulatory activity.

Depending on the use for contemplated conformationally constrained nucleosides the effective concentration (i.e. the concentration of the nucleoside in a system to achieve an effect in the system) of the nucleosides may vary considerably. For example, where the nucleosides are intracellularly employed to gene-specifically suppress expression the concentration may be as low as nM-fM and less within a cell, whereas in cases where contemplated nucleosides are utilized as enzyme inhibitors, the effective concentration may be in the $\mu M$ to mM range. Moreover, contemplated nucleosides may be employed in vitro (e.g., DNA- or RNA hybridization) or in vivo (e.g., modulation of immune system, antineoplastic agent). It is generally contemplated, however, that application and concentration ranges are similar to application and concentration ranges of D-nucleosides.

EXAMPLES

The following examples illustrate the synthesis of exemplary conformationally constrained L-nucleosides according to the inventive subject matter.

Example 1

Figure 3:
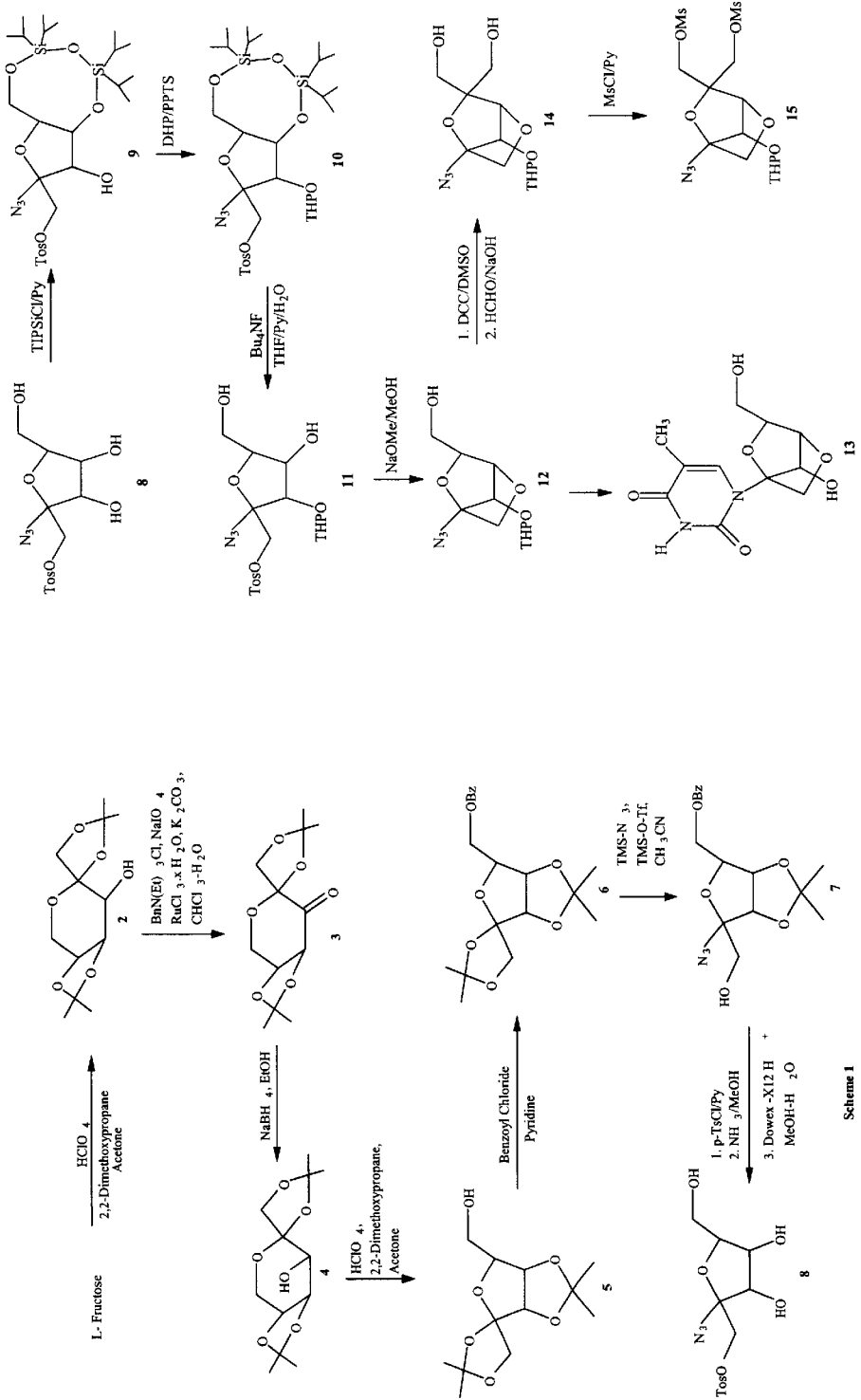
FIG. 3 shows a synthetic scheme of exemplary precursors for bicyclic and tricyclic conformationally constrained L-nucleosides according to the inventive subject matter.
Figure 4:
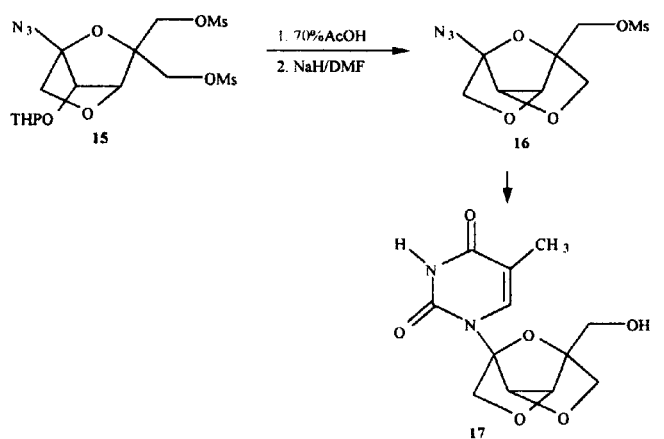
FIG. 4 shows a synthetic scheme of exemplary bicyclic and tricyclic conformationally constrained L-nucleosides according to the inventive subject matter.
Figure 4:
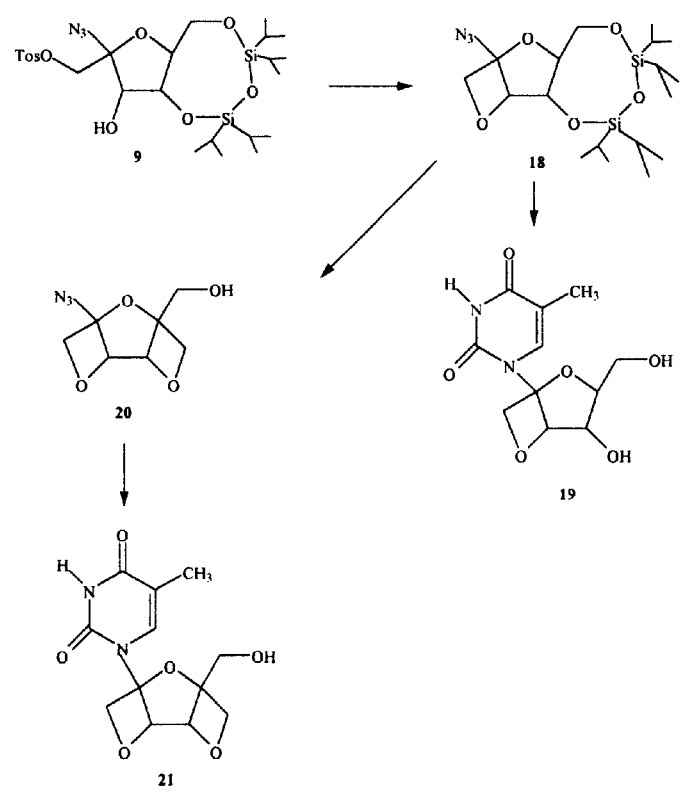

The following synthetic procedure illustrates the synthesis of an exemplary 1,3-bicyclic L-nucleoside and an exemplary 1,3:2,4-tricyclic L-nucleoside, and is depicted in FIGS. 3–4.

1,2:4,5-Di-O-isopropylidene-L-fructopyranose (2). 70% perchloric acid (4.3 ml, 48 mmol) was added at 0° C. to a suspension of L-fructose (1 8.42 g, 100 mmol) in a mixture of acetone (350 ml) and 2,2-dimethoxypropane (7.4 ml, 60 mmol), and the mixture was stirred for 6 h. To this mixture, concentrated ammonium hydroxide (4.8 ml) was added and the mixture was evaporated leading to a crystalline residue, which was dissolved in $CH_2Cl_2$ (200 ml). The solution was washed with brine (3×100 ml), dried ($Na_2SO_4$) and evaporated. The residue was crystallized from $CH_2Cl_2$ into hexane to give 2 (15.15 g 58%) as white needles.

1,2:4,5-Di-O-isopropylidene-L-erythro-2,3-hexodiuro-2,6-pyranose (3). $RuCl_3.H_2O$ (1.04 g, 4.6 mmol) was added to a mixture of 2 (35 g, 134 mmol), $PhCH_2(Et)_3NCl$ (1.53 g, 6.73 mmol $NaIO_4$ (42.7 g, 200 mmol) and $K_2CO_3$ (2.85 g, 20.6 mmol) in $CHCl_3$–$H_2O$ (1:1, 250 ml). The reaction temperature was gradually elevated to reflux. After 2 h, 2-propanol (40 ml) was added. The mixture was stirred for 1 h and then filtered through Celite. The organic layer was separated and the water layer was extracted with $CH_2Cl_2$ (2×100 ml). The combined organic layer was washed with saturated $Na_2SO_3$ (100 ml), water (100 ml), brine (100 ml) and dried ($Na_2SO_4$). Evaporation of the solvent gave 3 (34 g, 99%) as a white solid.

1,2:4,5-Di-O-isopropylidene-L-psicopyranose (4). To a solution of 3 (8.32 g, 32.2 mmol) in ethanol (80 ml) was added $NaBH_4$ (0.61 g, 16.2 mmol) at 15° C. After 1 h, the solvent was removed under reduced pressure. Ether (100 ml) and saturated NH$_4$Cl (30 ml) were added to the residue and stirred for 4 h. The mixture was partitioned between ether (200 ml) and water (100 ml) and the water layer was extracted with ether (3×50 ml). The combined ether extract was dried (Na$_2$SO$_4$) and evaporated to give 4 (8 g, 96%) as a white solid.

1,2:3,4-Di-O-isopropylidene-L-psicofuranose (5). 70% perchloric acid (0.15 ml, 1.7 mmol) was added at 5° C. to a solution of 4 (2.6 g, 10 mmol) in a mixture of acetone (25 ml) and 2,2-di-meth (0.62 ml, 5 mmol). The mixture was stirred for 3 h. After concentrated ammonium hydroxide (0.3 ml) was added, the solvent was evaporated. The residue was partitioned between ether (100 ml) and water (50 ml) and the water layer was extracted with ether (3×50 ml). The combined extract was washed with brine, dried (Na$_2$SO$_4$) and evaporated. The residue was chromatographed on silica gel (EtOAc→hexane 1:6) to give 5 (1.8 g, 70%) as a white solid.

6-O-Benzoyl-1,2:3,4-di-O-isopropylidene-L-psicofuranose (6). To a solution of 5 (10.4 g, 40 mmol) in pyridine (100 ml), cooled to 5° C., benzoyl chloride (5.56 ml, 48 mmol) was slowly added and the reaction mixture warmed to room temperature. After 16 h it was quenched with ice-cold saturated NaHCO$_3$ solution. The volatiles evaporated and the residue obtained was dissolved in a mixture of ethyl acetate (400 ml) and water (150 ml). The aqueous layer was extracted with ethyl acetate (3×100 ml). The combined extract was washed with water (2×300 ml), brine (400 ml), dried (Na$_2$SO$_4$) and evaporated. The residue obtained was co-evaporated with toluene (100 ml) and then purified over silica gel chromatography to afford 6 (13.6 g, 93%).

6-O-Benzoyl-3,4-O-isopropylidene-2-azido-2-deoxy-β-L-psicofuranose (7). To a solution of 6 (13.5 g, 37 mmol) and azidotrimethylsilane (9.75, 74.13 mmol) in acetonitrile (150 ml), trimethylsilyltriflate (2 ml, 11.06 mmol) was added. After the mixture was stirred at 0° C. for 30 min and at room temperature for 1 h, ether (250 ml) and saturated NH$_4$Cl (50 ml) were added, and the mixture was stirred for 1 h to hydrolyze the silyl ether intermediates. The water layer was extracted with ether (2×75 ml) and the combined extract was washed with brine (200 ml), dried (Na$_2$SO$_4$) and concentrated under reduced pressure. The resulting residue was chromatographed on silica gel (EtOAc: hexane 1:3) to give a mixture (95:5) of β and isomers of 7 (11.68 g, 95%).

2-Azido-2-deoxy-1-O-p-toluenesluphonyl-β-L-psicofuranose (8). To a solution of 7 (13 g, 37.25 mmol) in pyridine (150 ml), p-toluenesulphonyl chloride (17.67 g, 92.68 mmol) was added. After 16 h at room temperature the reaction mixture was cooled in ice water, slowly quenched with a saturated NaHCO$_3$ solution, and further diluted with water (500 ml). The precipitated solids were filtered and washed with water (3×500 ml), dried over P$_2$O$_5$ at room temperature. The crude product obtained was carried forward without further purification. The dried crude product (12 g) was treated with methanolic ammonia (150 ml) at room temperature for 16 h. The volatiles evaporated and the residue was extracted with CHCl$_3$ (250 ml). The organic layer was washed with water (500 ml), brine (500 ml), dried (Na$_2$SO$_4$) and evaporated. The crude reaction mixture (9 g) was dissolved in a mixture of methanol (100 ml) and water (50 ml) and treated with Dowex—X12 H$^+$ resin (acidic). The suspension was heated at 50° C. for 16 h. The resin was filtered and the filtrate evaporated. The residue obtained was purified by flash silica gel chromatography (CHCl$_3$—MeOH 100:0 to 95:5) to afford 8 (8 g, 60% for 3 steps).

4,6-O-(1,1,3,3-Tetraisopropyldisiloxane-1,3-diyl)-2-azido-2-deoxy-1-O-p-toluenesulphon-yl-β-L-psicofuranose (9). A solution of 8 (8 g, 22.28 mmol) in pyridine (75 ml) was treated with 1,3-dichloro-1,1,3,3-tetraisopropyldisiloxane (9.4 ml, 29.37 mmol) and stirred at room temperature for 16 h. The reaction mixture was carefully quenched with saturated NaHCO$_3$ solution (100 ml) and the volatiles evaporated. The residue obtained was dissolved in a mixture of CHCl$_3$ (250 ml) and water (100 ml). The aqueous layer was extracted with CHCl$_3$ (3×50 ml). The combined organic extract was washed with water (2×250 ml), brine (200 ml), dried (Na$_2$SO$_4$) and evaporated. The solvent was evaporated to obtain the crude product 9 (13 g, 97%).

4,6-O-(1,1,3,3-Tetraisopropyldisiloxane-1,3-diyl)-3-tetrahydropyranyl-2-azido-2-deoxy-1-O-p-toluenesluphonyl-β-L-psicofuranose (10). A reaction mixture of 9 (5 g, 8.32 mmol), dihydropyran (6 ml, 65.75 mmol), pyridinium-p-toluenesulphonate (3.13 g, 12.45 mmol) in CH$_2$Cl$_2$ (100 ml) was heated at 40–45° C. under N$_2$ atmosphere for 4 h. The reaction mixture was quenched with saturated NaHCO$_3$ solution (50 ml) and further diluted with CH$_2$Cl$_2$ (200 ml). The organic layer was washed with water (2×100 ml), brine (150 ml), dried (Na$_2$SO$_4$) and evaporated to obtain the crude product 10 in quantitative yield (5.7 g).

3-Tetrahydropyranyl-2-azido-2-deoxy-1-O-p-toluenesluphonyl-β-L-psicofuranose (11). To a solution of 10 (5.7, 8.32 mmol, crude form) in a mixture of THF/pyridine/water (125 ml, 2.5:1.5:1) tetrabutylammonium fluoride (7.8 g, 24.72 mmol) was added. After 16 h at room temperature the volatiles evaporated and the residue was extracted with CHCl$_3$ (250 ml). The organic layer was washed with water (2×200 ml), brine (150 ml), dried (Na$_2$SO$_4$) and evaporated. The evaporation of solvent gave crude product, which was purified over flash silica gel chromatography to afford a diastereomeric mixture of tetrahydropyranyl ethers 11 (3.58 g. 97%).

1,4-Anhydro-3-tetrahydropyranyl-2-azido-2-deoxy-β-L-psicofuranose (12). To a solution of 11 (1.8 g, 4.06 mmol) in anhydrous MeOH (50 ml), a methanolic solution (4.63 M) of NaOMe (7ml, 32.5 mmol) was added. After 16 h at reflux, the volatiles evaporated and the residue was extracted with ether (100 ml). The ether layer was washed with water (50 ml), brine (100 ml), dried (Na$_2$SO$_4$) and evaporated. The residue obtained was purified over flash silica gel chromatography, which gave the product 12 (0.73 g, 62.6%).

4-Hydroxymethyl-1,4-anhydro-3-tetrahydropyranyl-2-azido-2-deoxy-β-L-psicofuranose (14). Compound 12 was oxidized with 1.1 equivalent of DCC in DMSO to provide the corresponding aldehyde. The aledyhde was allowed to stir with 37% formaldehyde solution in 2N NaOH solution at room temperature for 12 h and to yield 14.

Compound 14 was reacted with methanesulfonyl chloride (2.2 equiv) in the presence of pyridine to give the dimesylate 15. Exposure of 15 to 70% AcOH for 6 h, followed by heating in the presence of sodium hydride in dry DMF yielded the tricyclic sugar 16.

Compound 12 was transformed into the 1,3-bicyclic nucleoside 13 by following the procedure and the reagents used in A. Ezzitouni, P. Russ and V. E. Marquez, *J. Org. Chem.*, 62, 4870 (1997). In the same way, compound 16 was converted into the 1,3:2,4-tricyclic nucleoside 17.

Example 2

The following synthetic procedure illustrates the synthesis of an exemplary 1,2-bicyclic L-nucleoside and an exemplary 1,2:3,4-tricyclic L-nucleoside, and is depicted in FIG. 4.

Compound 9 (supra) was heated with sodium hydride in DMF for 12 h at 80° C. and worked up to give bicyclic sugar 18. Compound 18 was subsequently transformed to the 1,2-bicyclic nucleoside 19 using the same procedure as outlined above. Alternatively, compound 18 was transformed into tricyclic sugar intermediate 20 utilizing the same procedure described for the preparation of 16. Compound 20 was then transformed to the 1,2:3,4-tricyclic nucleoside 21 by following the procedure as indicated for the preparation of compound 17 (supra).

Example 3

Figure 5:
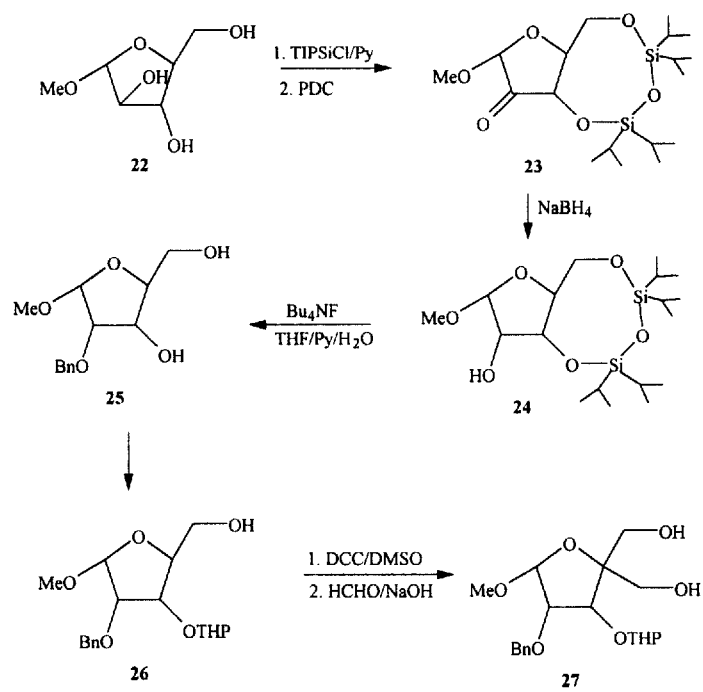
FIG. 5 shows a synthetic scheme of another exemplary bicyclic conformationally constrained L-nucleoside according to the inventive subject matter.
Figure 5:
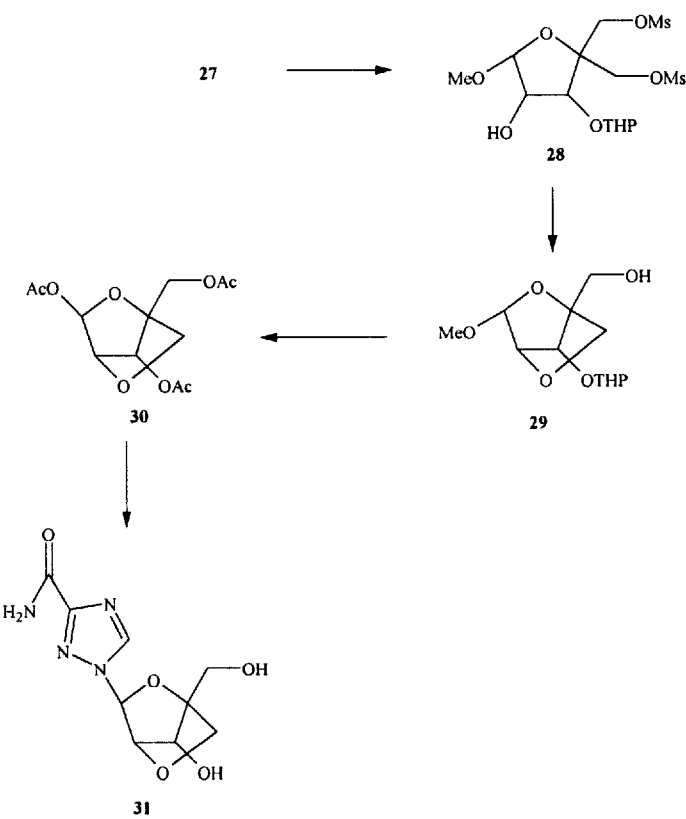

The following synthetic procedure illustrates the synthesis of an exemplary 2,4-bicyclic L-nucleoside and is depicted in FIG. 5.

2-C, 2-O-Didehydro-1-α-methyl-3-O, 5-O-(1,1,3,3-tetraisopropyldisiloxyl)-L-ribofuranose (23): To a stirred solution of 1-α-methyl-L-arabinose (22, 19.27 g, 119.9 mmol) in anhydrous pyridine (200 ml), 1,3-dichloro-1,1,3,3-tetraisopropyldisiloxane (38.4 ml, 119.9 mmol) was added at 0° C. The resulting solution was stirred at 0° C. for I h and then at room temperature overnight. The reaction mixture was evaporated to dryness and the residue was dissolved in EtOAc (400 ml). The organic extract was washed with water (200 ml) and brine (200 ml), dried, and concentrated to dryness to a colorless syrup. To a stirred solution of the above syrup (42.6 g, 104. 9 mmol) and DCC (43.4 g, 209.8 mmol) in anhydrous DMSO (250 ml) and ether (100 ml) at 0° C. under argon was added a solution of TFA (4.04 ml, 52.5 mmol) and pyridine (8.44 ml, 105 mmol) in DMSO (30 ml). The resulting reaction mixture was warmed up to room temperature, stirred at RT for 5 h, and then cooled to 0° C. Oxalic acid (21.3 g, 236 mmol) in methanol (60 ml) was added, followed by addition of water (30 ml). The resulting mixture was stirred at room temperature for 1 h, and the precipitate was filtered and washed thoroughly with hexanes. The filtrate was diluted with hexanes, washed with water (5×200 ml), dried and concentrated to dryness. The residue was purified by flash chromatography over silica gel using methylene→hexanes as the eluent to give 37.6 g (89%) as colorless syrup.

To a solution of 23 (8.32 g) in ethanol (80 ml), NaBH$_4$ (0.61 g) was added at 15° C. After 1 h, the solvent was removed under reduced pressure. Ether (100 ml) and sat. NH$_4$Cl (30 ml) were added to the residue and stirred for 4 h. The mixture was partitioned between ether (200 ml) and water (100 ml) and the water layer was extracted with ether (3×50 ml). The combined ether extract was dried (Na$_2$SO$_4$) and evaporated to give 8 g, (96%) of the product 24.

The product 24 was alkylated with benzyl bromide in the presence of NaH at RT for 8 h to provide the corresponding 2-benzyl derivative. The benzyl derivative on exposure to tetrabutylammonium fluoride gave deblocked sugar 25. Compound 25 was then reacted with tert-butyldimethylsilyl chloride and the crude product thus obtained was converted into a THP derivative under standard condition. Removal of the TBDMSi group from the THP derivative was achieved with tetrabutylammonium fluoride at room temperature to give 26.

To a stirred solution of the above syrup 26 (40 g) and DCC (43.4 g) in anhydrous DMSO (150 ml) at 10°C. under argon was added a solution of TFA (1.22 ml) and pyridine (2.9 ml) in DMSO (10 ml). The resulting reaction mixture was warmed up to room temperature, stirred at room temperature (RT) for 5 h, and then cooled to 0°C. After addition of water (10 ml), the reaction mixture was stirred overnight at RT. The precipitate was filtered and washed with EtOAc. The combined filtrate was washed with brine (5 ×100 ml), dried and concentrated to dryness. The residue was purified by flash chromatography over silica gel using methylene→hexanes as the eluent to give 35 g as colorless syrup.

To a stirred solution of the above residue and formaldehyde (37% in water 100 ml) in dioxane (250 ml) at 0° C. was added drop-wise 2N NaOH solution (100 ml) during 15 min. The resulting mixture was stirred at RT for 2 days. It was cooled to 0° C., neutralized to pH 8 with 10% AcOH and concentrated to a small volume. The aqueous solution was extracted with methylene chloride (3×250 ml). The organic layer was washed with brine, dried and concentrated to dryness. The residue was purified by flash chromatography over silica gel using methylene chloride→EtOAc as the eluent to give 27 as foam.

To a stirred solution of 27 (8.0 g) in dry pyridine (100 ml), methanesulfonyl chloride (4.0 ml) was added at 0° C. under argon. The resulting mixture was stirred at RT for 2 h and quenched with water (10 ml). The reaction mixture was evaporated to dryness and extracted with EtOAc. The organic extract was washed with water (100 ml) and brine, dried and concentrated to dryness. The residue in AcOH-water (80:20, 200 ml) was stirred at RT for 2.5 h and concentrated to half of its volume. It was extracted with EtOAc. The organic extract was evaporated to dryness and the residue purified over silica column chromatography to give a crude product which on hydrogenation with Pd/C in methanol at 45 psi of hydrogen afforded 28.

To a stirred mixture of NaH (1.83 g, 23.0 mmol) in dry THF (150 ml) was added a solution of 28 (5.20 g, 12.0 mmol) in dry THF (50 ml).The resulting reaction mixture was stirred at 60° C. for 48 h, quenched with water (5 ml) and evaporated to dryness. The residue was heated at reflux with aqueous NaOH (0.5 N, 200 ml) for 24 h, cooled to 0° C., neutralized with dilute HCl to pH 8 and extracted with methylene chloride (4×100 ml). The organic extract was washed with brine (100 ml), dried and evaporated to dryness. The residue was purified by flash chromatography over silica gel using methylene chloride→EtOAc as eluent to give 4.5 g of the pure product 29.

To a stirred mixture of 29 (5.0 g) in glacial AcOH (150 ml) and Ac$_2$O (30 ml) at 5° C. was added conc. H$_2$SO$_4$ (10 ml). The resulting reaction mixture was stirred at RT for 12 h and poured into crushed ice (500 g). It was stirred at RT for 1 h and extracted with EtOAc (2 ×150 ml). The organic extract was washed with brine (100 ml), dried and evaporated to dryness to give 4.0 g of the pure product 30.

(1S, 3R, 4R, 7S)-7-Hydroxy-1-hydroxymethyl-3-(3-carboxamide-1,2,4-triazol-1-yl)-2.5-dioxabicyclo[2.2.1] heptane (31). The 2,4-bicyclic L-nucleoside 31 will be prepared by fusion of compound 30 with methyl 1,2,4-triazole-3-carboxylate, followed by deblocking the acetyl protecting groups with methanolic ammonia employing the procedure reported in *J. Med. Chem.*, 15, 1150 (1972).

Example 4

Figure 6:
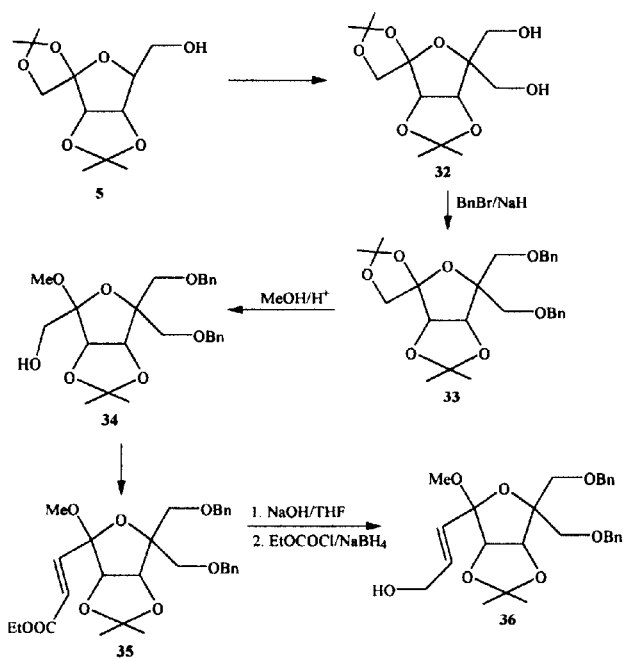
FIG. 6 shows a synthetic scheme of a further exemplary bicyclic conformationally constrained L-nucleoside according to the inventive subject matter.
Figure 6:
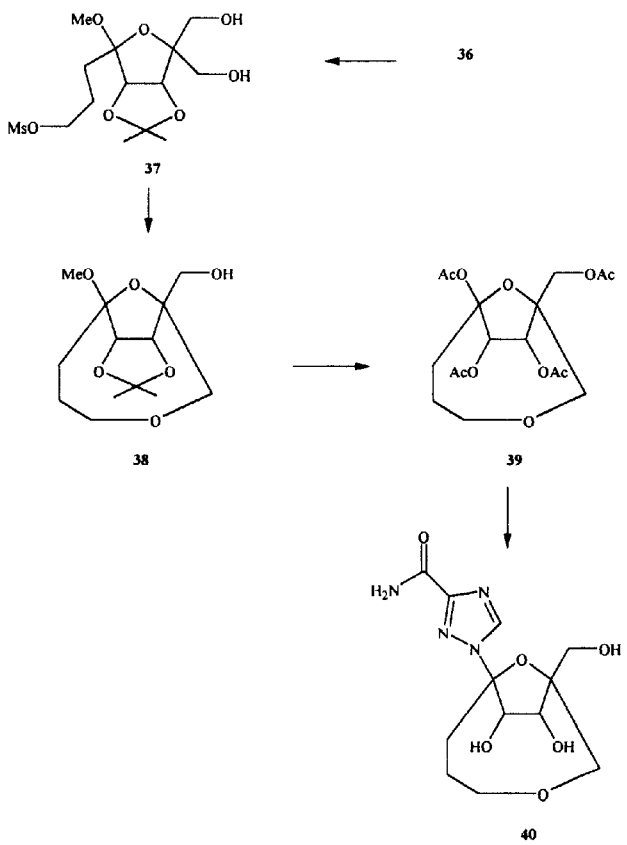
Figure 7:
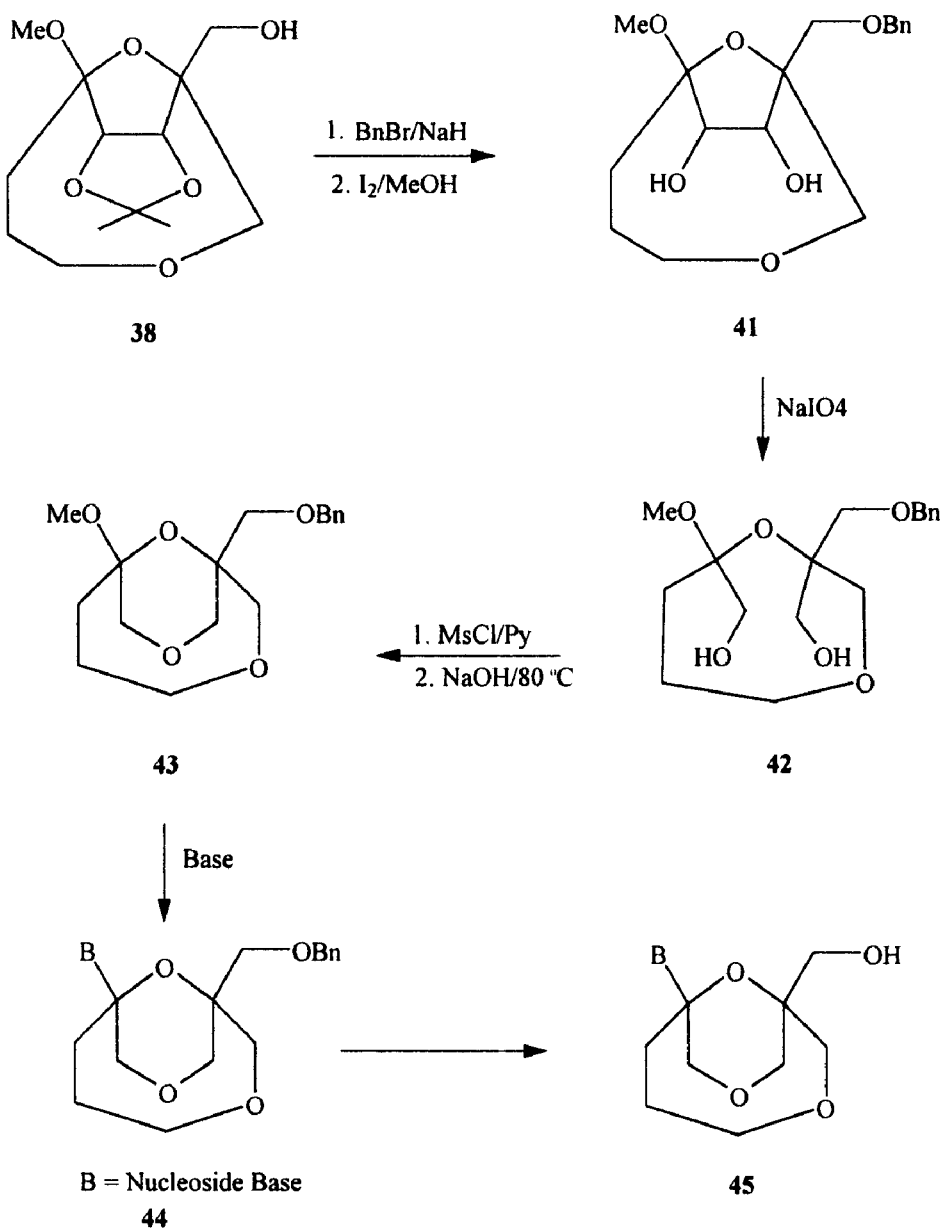
FIG. 7 shows a synthetic scheme of yet another exemplary bicyclic conformationally constrained L-nucleoside according to the inventive subject matter.

The following synthetic procedure illustrates the synthesis of exemplary 1,4-bicyclic L-nucleosides and is depicted in FIGS. 6–7.

To a stirred cold (--78° C.) solution of oxalyl chloride (17.5 ml, 200 mmol) in dry methylene chloride (400 ml) under argon atmosphere was added dry DMSO (28.5 ml, 400 mmol) in dry methylene chloride (40 ml) during 15–30 minutes period. After the addition of DMSO, the reaction was stirred for 20 min at −70° C. Compound 5 (40.0 g,. 153.85 mmol) in dry methylene chloride (50 ml) was added during 15 min period at −70° C. and stirred at that temperature for additional 30 min. Diisopropylamine ((138 ml, 800 mmol) was added during 20 min period at −70° C. and the reaction was allowed to stir at RT during 2 h period. The reaction mixture was washed with water (3×200 ml) and brine (200 ml), dried and evaporated to dryness to give 40 g of the crude product.

The crude product (40 g) was dissolved in dioxane (300 ml) and mixed with 37% formaldehyde (200 ml) at room temperature. The reaction was cooled to 0° C. to 5° C. To the cold solution was added 2N NaOH solution (200 ml) during 15–30 min period. After the addition of NaOH solution, the reaction mixture was allowed to stir at RT for 2 days and evaporated to 200 m in volume. The solution was extracted with methylene chloride (2×200 ml). The organic extract was washed with brine (200 ml), dried and evaporated to dryness. The residue was crystallized from EtOAc/hexanes as colorless crystals. The crystals were filtered and dried to give 42 g (94%) of 32.

To a stirred solution of 32 (5. 8 g, 20.00 mmol) in dry DMF (100 ml) at 0° C. was added NaH (40% in oil; 2.0 g, 50 mmol) during 30 min period. After the addition of NaH, the reaction was allowed to stir at RT for 1 h. Benzyl bromide (6.3 g, 50 mmol) was added during 10 min period and the reaction mixture stirred at RT for 12 h. It was evaporated to dryness and the residue was dissolved in EtOAc (200 ml), washed with water (100 ml) and brine (100 ml), dried and concentrated to dryness. The residue was crystallized from methanol to give 9.4 g (100%) of 33.

To a stirred solution of 33 (9.4 g) in dry MeOH (50 ml) at RT was added concentrated $H_2SO_4$ (1 ml). The reaction was allowed to stir at RT for 24 h, cooled to 0° C., neutralized with concentrated $NH_4OH$ (20 ml) and evaporated to dryness. The residue was dissolved in EtOAc (200 ml), washed with brine (100 ml), dried and concentrated to dryness. The residue was purified by flash chromatography over silica gel using $CHCl_3 \rightarrow EtOAc$ as the eluent to give 5.0 g (57%) of 34.

Oxidation of the 1'-hydroxylmethyl group of 34 with PDC in pyridine should provide the corresponding aldehyde, which on further treatment with ethoxycarbonylmethylenetriphenylphosphorane ($Ph_3P$=CHCOOEt) will afford 35. Basic hydrolysis of the ester group in 35 followed by reduction of the acid with ethylchloroformate and sodium-borohydride will give the alcohol 36. The hydroxyl group of 36 will subsequently be converted to a mesyl derivative by reaction of 36 with mesyl chloride in pyridine. The mesyl derivative on hydrogenation with Pd/C in methanol will then furnish the intermediate 37, which will be cyclized using the same conditions as described in preparation of compound 29 to give the product 38. Treatment of 38 with $Ac_2O$ and $H_2SO_4$ will provide the required bicyclic sugar 39. Acid fusion of 39 with methyl 1,2,4-triazole-3-carboxylate followed by deblocking of the protecting groups utilizing the conditions reported in Example 24 will yield the 1,4-bicyclic L-nucleoside 40.

Alternatively, compound 38 on alkylation with benzyl bromide in the presence of sodium hydride will provide 41, which on oxidation with sodium periodate will give 42. Treatment of 42 with methanesulfonyl chloride will afford the corresponding dimesylate intermediate. The dimesylate on heating with aqueous NaOH solution will furnish the bicyclic sugar 43. Using literature glycosylation procedure the nucleoside of type 44 will be synthesized. The alternative 1,4-bicyclic L-nucleoside 45 will be accomplished by the removal of benzyl group from 44 with Pd/C.

Thus, specific embodiments and applications of conformationally constrained nucleosides and oligonucleotides have been disclosed. It should be apparent, however, to those skilled in the art that many more modifications besides those already described are possible without departing from the inventive concepts herein. The inventive subject matter, therefore, is not to be restricted except in the spirit of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced.

What is claimed is:

1. A nucleoside having a nucleobase glycosidically bound to a sugar moiety wherein the sugar. moiety has an L-configuration and has at least one additional ring that is formed via a bridge connecting a first and a second atom in the sugar moiety, wherein the first and the second atom are separated by at least a third atom in the sugar moiety.

2. The nucleoside of claim 1 having the structure:

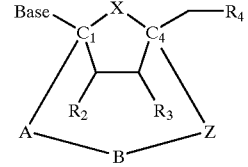

wherein Base is a nucleobase covalently bound to the $C_1$-atom via a nitrogen- or carbon atom in the nucleobase;

X is O, S, CHOH, $CH_2$ or N—$COCH_3$;

A is O, S, $(CH_2)_n$, N—R, or nothing, and when both B and Z are independently O, S or N—R then A is $(CH_2)_n$, wherein R is H, OH, CO—, $OPO_3^{2-}$, lower alkyl or $COCH_3$, and n is 1–5;

B and Z are independently O, S, $(CH_2)_n$, or N—R, and when both A and B are independently O, S or N—R then Z is $(CH_2)_n$, wherein R is H, OH, CO—, $OPO_3^{2-}$, lower alkyl or $COCH_3$, and n is 1–5;

wherein no more than two of A, B, and Z are an atom other than a carbon atom; and $R_2$ and $R_3$ are independently H, OH, $OPO_3^{2-}$, CN, halogen, $N_3$, $CH_2OH$, methylidene, lower alkyl or lower alkyl amine, and $R_4$ is H, OH, $OPO_3^{2-}$.

3. The nucleoside of claim 2 wherein the nucleoside is covalently coupled to at least one nucleotide, and wherein the covalent coupling involves at least one of $R_2$, $R_3$, $R_4$, and B.

4. The nucleoside of claim 3 wherein the nucleoside is covalently coupled to an oligonucleotide to form a modified oligonucleotide.

5. The nucleoside of claim 4 wherein the coupling to the oligonucleotide is on at least one of a 5'-end and a 3'-end of the oligonucleotide.

6. The nucleoside of claim 3 wherein the nucleoside is covalently coupled to a mononucleotide to form a modified dinucleotide.

* * * * *